United States Patent
Bottman

(10) Patent No.: US 9,429,534 B2
(45) Date of Patent: Aug. 30, 2016

(54) METHOD AND APPARATUS FOR DETERMINING WIRE RESISTANCE

(71) Applicant: Jeffrey Sandsmark Bottman, Seattle, WA (US)

(72) Inventor: Jeffrey Sandsmark Bottman, Seattle, WA (US)

(73) Assignee: Fluke Corporation, Everett, WA (US)

( * ) Notice: Subject to any disclaimer, the term of this patent is extended or adjusted under 35 U.S.C. 154(b) by 777 days.

(21) Appl. No.: 13/896,031

(22) Filed: May 16, 2013

(65) Prior Publication Data

US 2014/0340101 A1    Nov. 20, 2014

(51) Int. Cl.
  *G01R 27/08* (2006.01)
  *G01N 27/04* (2006.01)
  *H04B 3/46* (2015.01)

(52) U.S. Cl.
  CPC .............. *G01N 27/04* (2013.01); *H04B 3/46* (2013.01)

(58) Field of Classification Search
  CPC .................. H01L 2224/48091; H01L 25/167; G01R 31/31708; G01R 33/02; G01V 3/087
  USPC ........ 324/210–212, 690–693, 537, 700–718, 324/500, 600, 509, 536, 426, 525, 627, 551
  See application file for complete search history.

(56) References Cited

U.S. PATENT DOCUMENTS

| | | | |
|---|---|---|---|
| 2006/0069971 A1* | 3/2006 | Waschura | H04L 1/24 714/724 |
| 2013/0127481 A1* | 5/2013 | Vladan | G01R 27/16 324/713 |

OTHER PUBLICATIONS

Extended European Search Report for European Patent No. 14168547.9 dated Aug. 14, 2014.
"Measuring Resistance Imbalance Between Two Conductors of a Pair", Jul. 1, 2002, pp. 1-3, XP055133700. Retrieved from the Internet: URL:http://www.aemc.com/techinfo/appnotes/megohm-meters/APP-Megohm-TelephoneCables.pdf.

* cited by examiner

*Primary Examiner* — Melissa Koval
*Assistant Examiner* — Trung Nguyen
(74) *Attorney, Agent, or Firm* — Locke Lord LLP; Scott D. Wofsy; Christopher J. Capelli

(57) ABSTRACT

A method and apparatus qualifies a conductor for service and determines imbalance resistance of a conductor. The method and apparatus comprises feeding signals from a controller to termination ends of at least three wires of a conductor. In the controller a resistance difference is determined between first and second wires of the conductor using a measured resistance of one of the three conductor wires as a reference value. The conductor is qualified for services when the resistance difference between the first and second wires is below a threshold.

12 Claims, 4 Drawing Sheets

METHOD AND APPARATUS FOR DETERMINING WIRE RESISTANCE

FIELD OF THE INVENTION

The invention generally relates to communication networks, and more particularly, to a method and system for determining resistance imbalance in communications cables.

BACKGROUND OF THE INVENTION

Enterprise workspace is quickly evolving with new networked devices to improve communication, collaboration, security, and productivity. Power over Ethernet (PoE), a way to deliver electrical power over LAN cabling to networked devices, has been widely deployed over the years to provide power to various endpoints in the enterprise workspace environment using existing conductors. In recent years, Power Over Ethernet (PoE) standards and equipment have been developed that utilize the twisted pairs to transmit DC power in addition to data. End user PoE equipment, such as telephones and video cameras, are conveniently powered through the ethernet jack, thus eliminating the need for a local AC power outlet.

PoE systems typically transmit electrical power by using one twisted pair of a datacomm cabling system containing four twisted pair communication channels to send current to equipment, and another pair to return the current to the power source. Each pair is also typically connected to ferrite core transformers (baluns) that convert the differential twisted pair signal to a single ended signal for subsequent processing. PoE current flows through the transformer windings with each wire preferably carrying half of the current. The two currents induce equal and opposite DC flux in the transformer ferrite core, resulting in cancellation and no DC flux. It is to be appreciated that any remnant DC flux can degrade the transformer's performance due to core saturation resulting in possible degradation of data transmission.

It is to be appreciated that if the two conductors in a pair have equal resistance, along with the transformer coils, a 50/50 current split is assured, and transformer saturation will not occur. However, Ohm's law dictates that a significant resistance difference will result in current imbalance and possibly core saturation. As one skilled in the art appreciates, limits have been established for maximum acceptable resistance imbalance in the data communication channel. Therefore, there is a need for qualifying a conductor for data services and to determine imbalance resistance of the conductor.

SUMMARY OF THE INVENTION

The purpose and advantages of the invention will be set forth in and apparent from the description that follows. Additional advantages of the invention will be realized and attained by the devices, systems and methods particularly pointed out in the written description and claims hereof, as well as from the appended drawings.

To achieve these and other advantages and in accordance with the purpose of the invention, as embodied, the invention includes, in one aspect, a method and apparatus for qualifying a conductor for services and to determine imbalance resistance of the conductor. The method and apparatus comprises feeding signals from a controller to termination ends of at least three wires of a conductor, then determining in the controller a resistance difference between first and second wires of the conductor using a measured resistance of one of the three conductor wires as a reference value. The conductor is qualified for services when the resistance difference between the first and second wires is below a threshold.

Another aspect of the invention relates to determining imbalance resistance of a conductor having at least three wires by first determining a resistance value of a first wire loop consisting of an aggregate resistance of any two of the at least three conductor wires. Next, a resistance value of a second wire loop is determined, with the loop consisting of an aggregate resistance of one of the wires used in determination of the first loop and a conductor wire not used in determination of the first wire loop. A resistance difference is then determined between the first and second wire loops. And intra-pair resistance imbalance is determined for the conductor according to the determined resistance difference.

Another aspect of the invention relates to an apparatus and method to measure single wire resistance in a communication cable having at least first and second wire pairs. The method and apparatus comprises first measuring resistance between a first wire of a first wire pair and one reference wire chosen from a second wire pair to produce a first loop resistance measurement value. Next, resistance between a second wire of the first wire pair and the reference wire is measured to produce a second loop resistance value. Next, resistance between the first wire and the second wire of the first wire pair is measured to produce a third loop resistance measurement value. Resistance of the first wire is determined by calculating a resistance sum value by adding the third loop value to a difference between the first and second loop values and dividing the resistance sum value in half.

In further, optional aspects, in the foregoing method and apparatus the aforementioned services comprise low-voltage DC power transmission. Each of the first and second wires may be constituents of a twisted pair of wires. The resistance of each wire is determined by measuring the resistance at one end of the wire while the other end of the wire is coupled to the controller. The aforementioned communication cable may be a twisted pair datacomm cable. Additionally, at least one of the wires used in the loop measurement determinations may be a wire shield. An embodiment of the invention can implement one or more of these optional aspects.

BRIEF DESCRIPTION OF THE DRAWINGS

The accompanying appendices and/or drawings illustrate various non-limiting, example, inventive aspects in accordance with the present disclosure.

DETAILED DESCRIPTION OF CERTAIN EMBODIMENTS

Figure 1:
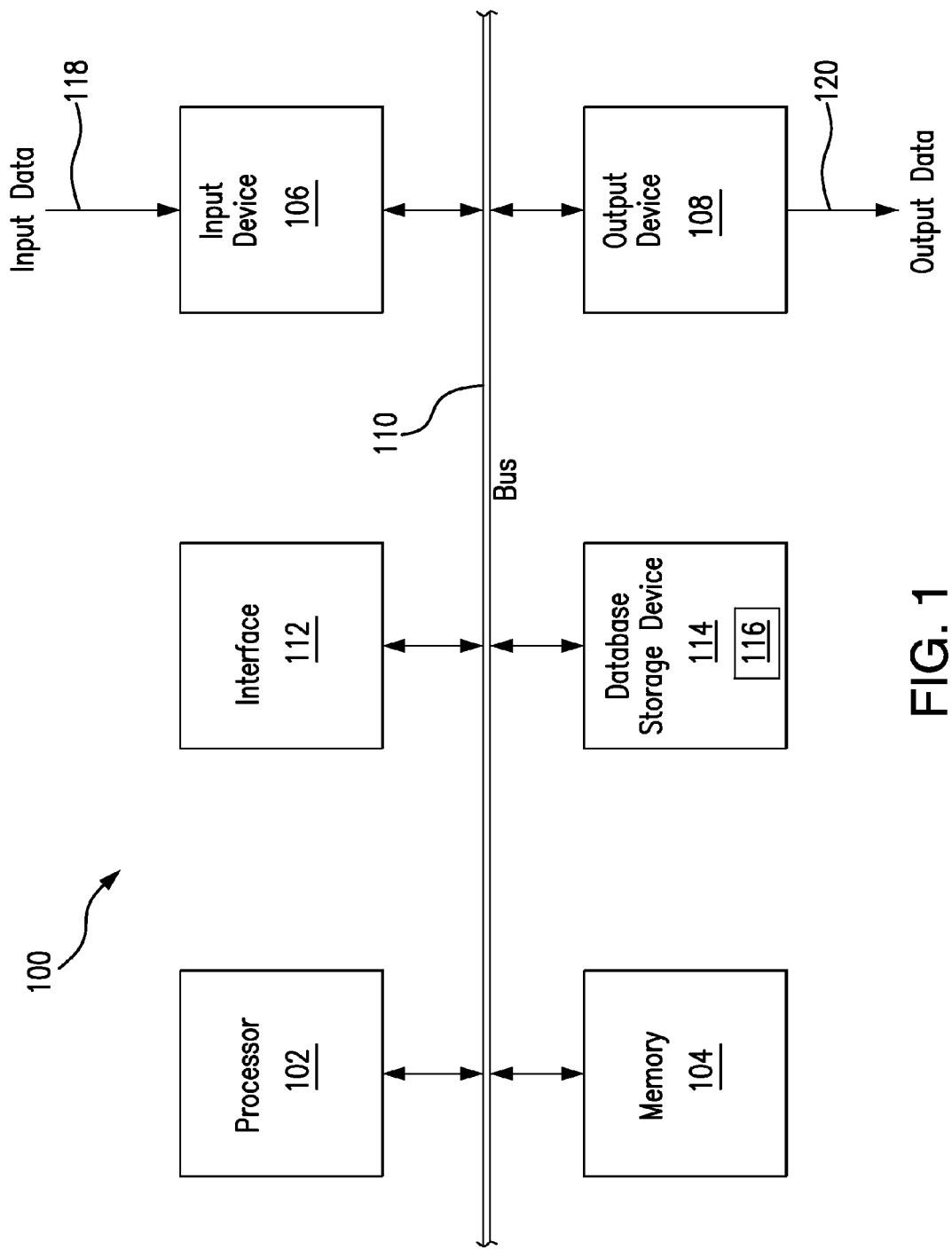
FIG. 1 illustrates a system overview and data-flow in one embodiment of system operation.

The present invention is now described more fully with reference to the accompanying drawings, in which an illustrated embodiment of the present invention is shown. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the embodiments of this invention as discussed below are preferably a software algorithm, program or code residing on computer usable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Turning now descriptively to the drawings, in which similar reference characters denote similar elements throughout the several views, FIG. 1 depicts an exemplary general-purpose computing system in which illustrated embodiments of the present invention may be implemented.

It is to be understood the present invention is to be used in a generalized computing embodiment in which the present invention can be realize. This embodiment is depicted in FIG. 1 illustrating a processing system 100 which generally comprises at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. Preferably, the processor 102 receives instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN), but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which embodiments of the below described present invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, tablet devices, smart phone devices, multiprocessor systems, microprocessor-based systems, set top boxes, programmable consumer electronics, network, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1 being generally shown and discussed above, discussion will now turn to the present invention apparatus and method for determining wire resistance which utilizes computer system 100, or components thereof.

Figure 2:
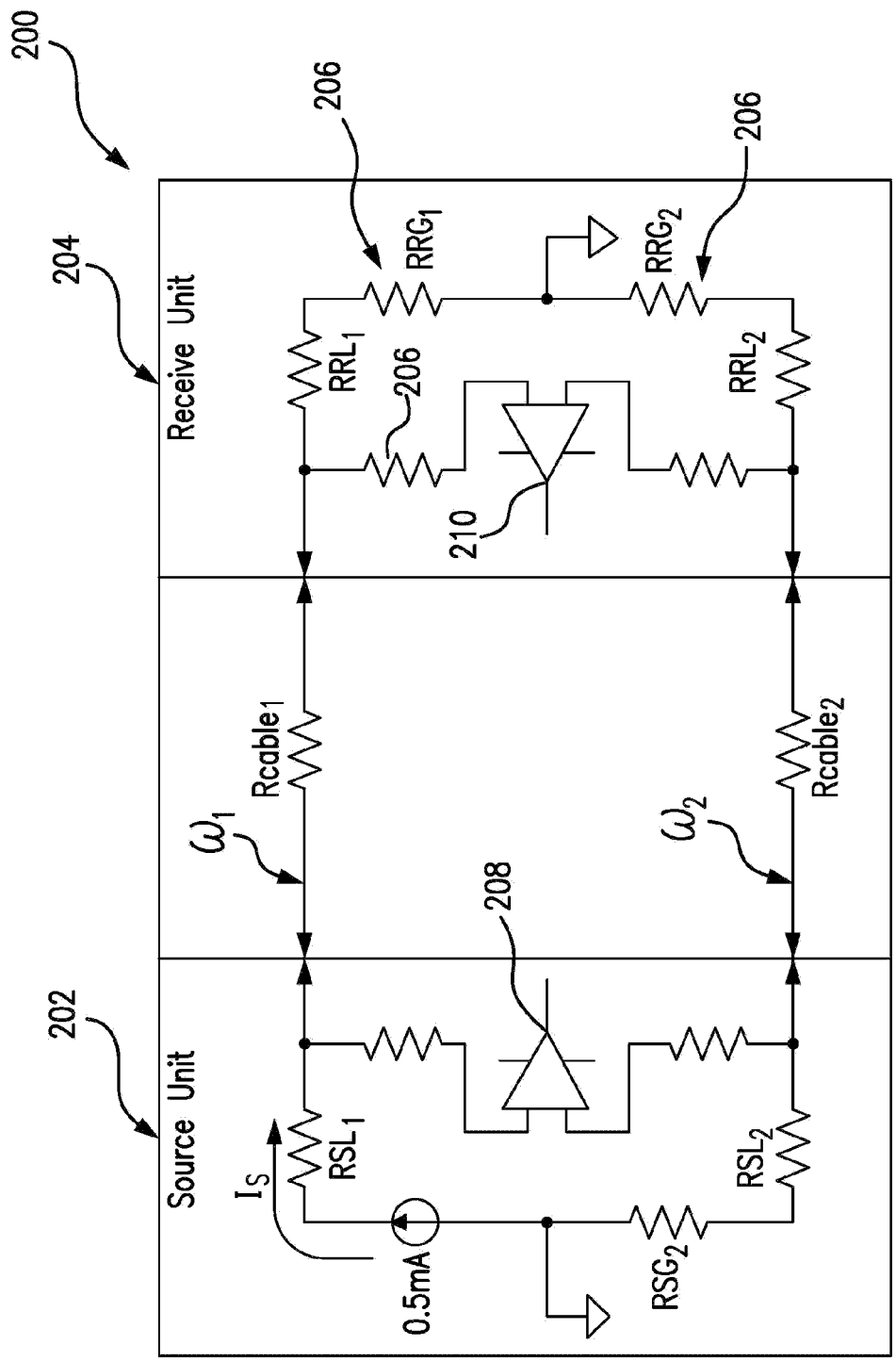
FIG. 2 illustrates an apparatus for measuring cable pair loop resistance in accordance with the present invention.

With reference now to FIG. 2, and in accordance with an illustrated embodiment, an apparatus is shown for measuring cable pair loop resistance designated generally by reference numeral 200. Apparatus 200 preferably includes a source unit 202 and a receive unit 204. The source unit 202 is preferably adapted and configured to provide current excitation. The receive unit 204 is preferably adapted and configured to provide a current path between the wires ($W_1$ and $W_2$) of the cable pair through preferably programmable grounding resistors 206. Preferably, both the source unit 202 and the receive unit 204 measure the resulting voltage at the points where amplifiers 208 and 210 are coupled to the wires ($W_1$ and $W_2$) of the cable. It is to be appreciated that to facilitate loop measurement, a far-end tester (e.g., receive unit 204) completes the loop by preferably routing a current from a source wire to a receive wire so as to measure the resistance of the current path.

It is to be understood a loop resistance is obtained by the resistance measured by the source unit 202 subtracting the resistance measured by the receive unit 204. The loop resistance of the two wires ($W_1$ and $W_2$) of a twisted pair to be measured is:

Rcable1+Rcable2.

Figure 3:
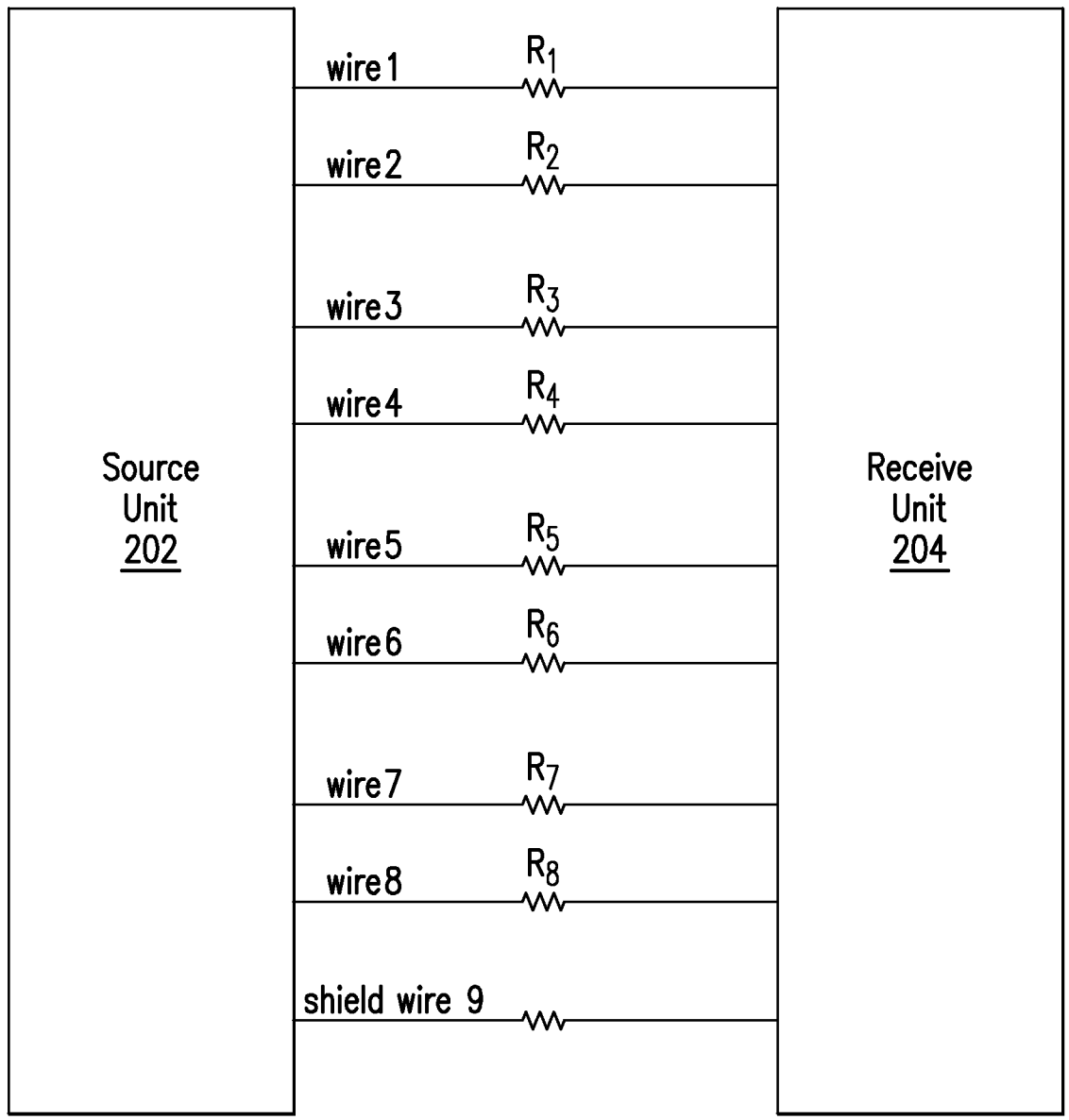
FIG. 3 is schematic illustration of an apparatus for measuring resistance imbalance of a PoE communication cable according to an illustrated embodiment of the present invention.

With reference now to the illustrated embodiment of FIG. 3, discussion will now be provided regarding measurement of resistance imbalance for a Power over Ethernet (PoE) cable. It is to be appreciated a PoE cable typically consists of eight wires (wires 1 to 8), forming four pairs of twisted wires. FIG. 3 additionally depicts an optional $9^{th}$ conductor (shield wire 9), which is present in Shielded Twisted Pair systems. As shown in FIG. 3 the first twisted pair is formed by wire 1 and wire 2, the second twisted pair is formed by wire 3 and wire 4, the third twisted pair is formed by wire 5 and wire 6 and the fourth twisted pair is formed by wire 7 and wire 8.

As shown in FIG. 3, the resistance of wire 1 is R1, the resistance of wire 2 is R2 carrying through to the resistance of wire 8 which is R8. According to an illustrated embodiment of present invention, the loop resistance is determined by measuring the resistance by the source unit 202, and then subtracting the resistance measured by the receive unit 204.

It is to be understood that prior to determining the differential resistance, it is preferable to verify that the cable under test is wired correctly. Therefore, and in accordance with an illustrated embodiment, the differential resistance of wire 1 and wire 2 can be determined by the loop resistance of wire 1 and wire 3 and the loop resistance of wire 2 and wire 3. As shown in the following formula, the differential resistance between wire 1 and wire 2 (R1−R2) can be determined by corresponding loop resistances measured:

$$(R1+R3)-(R2+R3)=R1+R3-R2-R3=R1-R2$$

As indicated above, to measure the differential resistance of wire 1 and wire 2 (R1−R2), the resistance of the loop formed by wire 1 and wire 3 (R1+R3) is measured and the resistance of the loop formed by wire 2 and wire 3 (R2+R3) is then subtracted from this measurement.

Similarly, and as shown in the below formulas, the differential resistance of wire 2 and wire 3 (R2−R3) can be determined by subtracting the loop resistance of wire 1 and wire 3 (R1+R3) from the loop resistance of wire 1 and wire 2 (R1+R2). Likewise, the differential resistance of wire 3 and wire 1 (R3−R1) is determined by subtracting the loop resistance of wire 1 and wire 2 (R1+R2) from the the loop resistance of wire 2 and wire 3 (R2+R3):

$$(R1+R2)-(R1+R3)=R1+R2-R1-R3=R2-R3$$

$$(R2+R3)-(R1+R2)=R2+R3-R1-R2=R3-R1$$

It is to be appreciated that by the measurement method described above, resistance imbalance can be determined according to differential resistance. In accordance with an illustrated embodiment, a computer processor preferably 102 compares the differential resistance as measured with reference to a threshold value. If the differential resistance exceeds the threshold value, the processor 102 preferably generates a resistance imbalance signal, which is sent to an output device 108 to indicate this condition to a user. Otherwise, if the differential resistance is below the threshold value, an indication is provided to a user, via preferably processor 102 and output device 108, indicating that the conductor qualifies for the desired service(s). For instance, such desired service can included (but is not to be understood to be limited thereto) to low-voltage DC power transmission.

Figure 4:
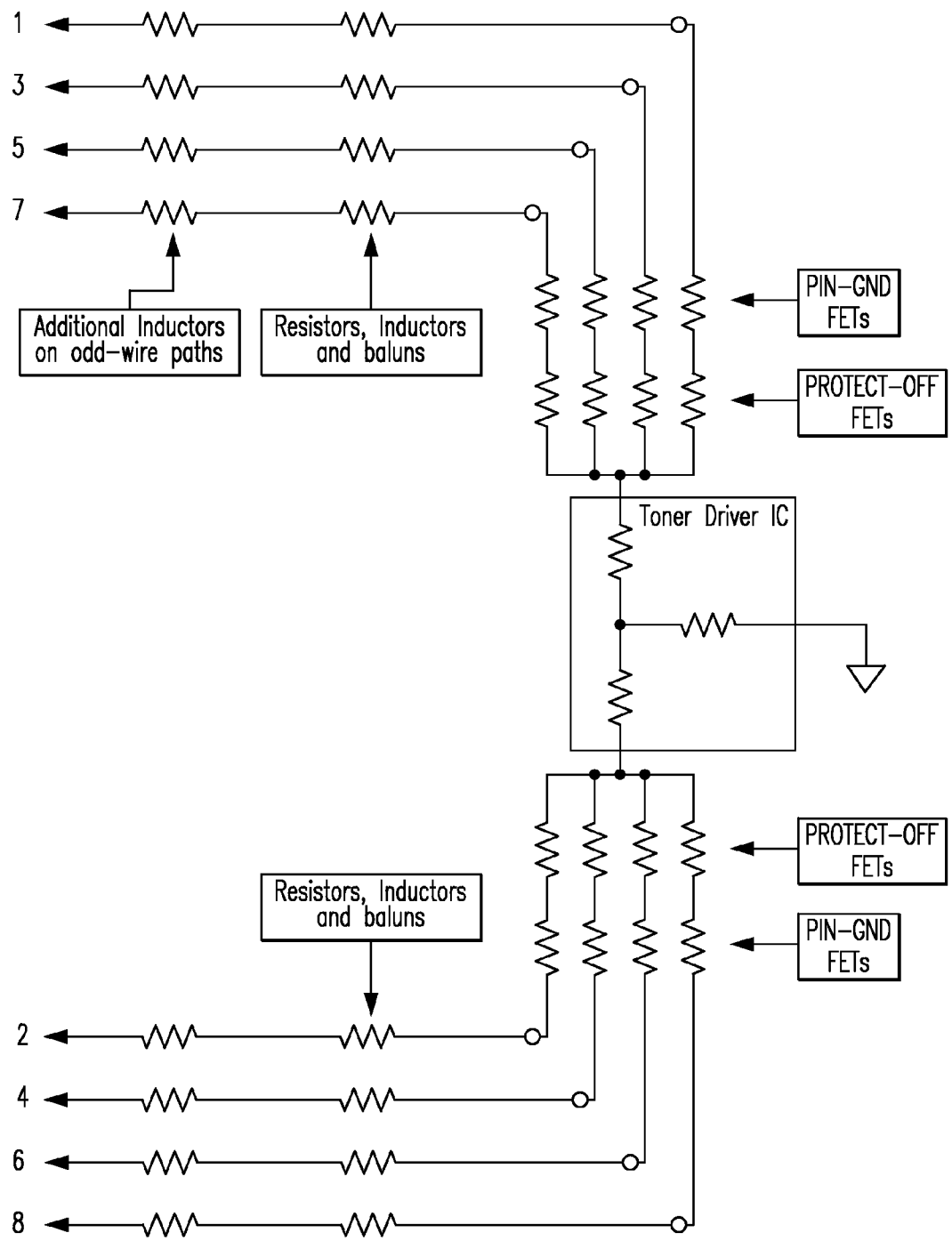
FIG. 4 is schematic illustration of an apparatus for determining average values of resistive components of various loop-completing paths in accordance with an illustrated embodiment of the invention.

Alternatively, and in accordance with another illustrated embodiment, differential resistance can be determined by an average value of resistive components of the various loop-completing paths on the far-end tester, as shown in FIG. 4. For instance, for the pair of wire 1 and wire 2, the following loop combinations can be used:

$$R1 - R2 = (R1 + R3) - (R2 + R3)$$
$$= (R1 + R6) - (R2 + R6)$$
$$= (R3 + R1) - (R3 + R2)$$
$$= (R6 + R1) - (R6 + R2)$$

It is appreciated that loop resistance (R3+R1) is the reverse current version of (R1+R3) and the loop resistance (R6+R1) is the reverse current version of (R1+R6). The differential resistance between wire 1 and wire 2 is an average value of the four sets resistance values measured. Preferably, the four loop resistance measurement can also repeat, with the roles of the source and receive units reversed, so the final differential resistance value between wire 1 and wire 2 is an average value of 8 sets of measurements. Similarly, the differential resistance value between wire 3 and wire 6 is measured using:

$$R3 - R6 = (R1 + R3) - (R1 + R6)$$
$$= (R2 + R3) - (R2 + R6)$$
$$= (R3 + R1) - (R6 + R1)$$
$$= (R3 + R2) - (R6 + R2)$$

The differential resistance value between wire 5 and wire 4 is measured using:

$$R5 - R4 = (R5 + R7) - (R4 + R7)$$
$$= (R5 + R8) - (R4 + R8)$$
$$= (R7 + R5) - (R7 + R4)$$
$$= (R8 + R5) - (R8 + R4)$$

The differential resistance value between wire 7 and wire 8 is measured using:

$$R7 - R8 = (R4 + R7) - (R4 + R8)$$
$$= (R5 + R7) - (R5 + R8)$$
$$= (R7 + R4) - (R8 + R4)$$
$$= (R7 + R5) - (R8 + R5)$$

According to yet another illustrated embodiment of the present invention, resistance values, and resistance imbalance, for each of the conductor wires is determined by comparing the resistance of each of the conductor wires. For instance, and with returning reference to FIG. 3, resistance of each of the conductor wires is determined by a corresponding differential resistance and loop resistance, as shown in the following formula:

$$R1=1/2*[(R1-R2)+(R1+R2)]$$

$$R2=1/2*[(R2-R3)+(R2+R3)]$$

$$R3=1/2*[(R3-R1)+(R1+R3)]$$

For example, resistance of wire 1(R1) can be determined by the differential resistance between wire 1 and wire 2 (R1−R2) and the loop resistance of wire 1 and wire 2 (R1+R2). Similarly, resistance of wire 2 (R2) can be determined by the differential resistance between wire 2 and wire 3 (R2−R3) and the loop resistance of wire 2 and wire 3 (R2+R3). It is to be appreciated and understood that resistance of wire 4 to wire 8 is measured by the same method as described above. By this measurement method, resistance of each wire can be obtained. The processor 102 then preferably compares the resistance of each wire and resistance imbalance is determined by the comparison result.

Alternatively, the resistance of each wire can also be determined by corresponding loop combinations. For example, for wire 1, wire 2 and wire 3, resistance can be determined by the following formula, respectively:

$$R1=1/2*[(R1+R3)-(R2+R3)+(R1+R2)]$$

$$R2=1/2*[(R2+R3)-(R1+R3)+(R1+R2)]$$

$$R3=1/2*[(R1+R3)-(R1+R2)+(R2+R3)]$$

As indicated above, resistance for wire 1 (R1) is determined by measuring resistance between the first wire of the first wire pair (wire 1) and one reference wire chosen from the second wire pair (wire 3) to produce a first loop resistance measurement value (R1+R3), and resistance between a second wire of the first wire pair (wire 2) and the reference wire (wire 3) can be measured as a second loop resistance measurement value (R2+R3), and resistance between the first wire (wire 1) and the second wire (wire 2) of the first wire pair can be measured to obtain a third loop resistance measurement value (R1+R2). After these loop resistances have been measured, the resistance of the first wire (R1) can be determined by calculating a resistance sum value by adding the third loop value (R1+R2) to a difference between the first and second loop values (R1+R3)−(R2+R3), and then the resistance sum value is divided in half to obtain a final resistance of wire 1 (R1). It is thus to be understood and appreciated that the resistance of each wire for the communication cable is determined in the similar method. It is to be further appreciated that the processor 102 then compares the resistance of each wire. Resistance imbalance is determined by the comparison result.

It is to be further appreciated and understood that a wire shield may be used as the reference wire if the cable is shielded. Preferably, in the current described illustrated embodiment, when measuring differential resistance, a higher current is applied, for instance, 8.57 ma. In contrast, when measuring loop resistance, a lower current is applied, for instance, 0.5 ma. This current has to be more accurately controlled, so the differential resistance measurement algorithm assumes that the calibration of the main and remote unit is sufficiently accurate with either the main or the remote unit providing the measurement current. In accordance with an illustrated embodiment, the present invention uses a loop resistance measurement system that is adapted to allow measurement of any two of the nine conductors connecting the main and remote units in a loopback configuration. The nine conductors are the 8 conductors for the 4 pairs, plus the shield, if there is one (cable can be shielded or unshielded). Thus, non-pair loops can be measured.

The above presents a description of a best mode contemplated for carrying out the present invention and of the manner and process of making and using it in such full, clear, concise, and exact terms as to enable any person skilled in the art to which it pertains to make and use these devices and methods. The present invention is, however, susceptible to modifications and alternative method steps from those discussed above that are fully equivalent. Consequently, the present invention is not limited to the particular embodiments disclosed. On the contrary, the present invention encompasses all modifications and alternative constructions and methods coming within the spirit and scope of the present invention.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function, it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method of qualifying a conductor for services, wherein the conductor has at least three wires, comprising the steps of:
   feeding signals from a controller to termination ends of at least three wires of the conductor;
   determining in the controller:
      a resistance difference between first and second wires of the conductor using a measured resistance of one of the three conductor wires as a reference value;
      resistance values for each of the at least three conductor wires;
      a resistance value of a first wire loop consisting of an aggregate resistance of any two of the at least three conductor wires; and
      a resistance value of a second wire loop consisting of an aggregate resistance of one of the wires used in determination of the first loop and a conductor wire not used in determination of the first wire loop; and
   qualifying the conductor for services when the resistance difference between the first and second wires is below a threshold.

2. A method as recited in claim 1 wherein the services comprise low-voltage DC power transmission.

3. A method as recited in claim 1 wherein each of the first and second wires are constituents of a twisted pair of wires.

4. A method as recited in claim 1, further comprising the step of determining in the controller a difference in resistance values between the first and second wire loops.

5. A method as recited in claim 1 wherein the resistance of each wire is determined by measuring the resistance at one end of the wire while the other end of the wire is coupled to the controller.

6. An apparatus to measure wire resistance in a communication cable having at least first and second wire pairs, comprising:
   a memory;
   a processor disposed in communication with the memory, and configured to issue a plurality of instructions stored in the memory, wherein the instructions issue signals to:
   measure resistance between a first wire of the first wire pair and one reference wire chosen from the second wire pair to produce a first loop resistance measurement value;
   measure resistance between a second wire of the first wire pair and the reference wire to produce a second loop resistance measurement value;
   measure resistance between the first wire and the second wire of the first wire pair to produce a third loop resistance measurement value; and
   determine resistance of the first wire by calculating a resistance sum value by adding the third loop value to a difference between the first and second loop values; and dividing the resistance sum value in half.

7. An apparatus as recited in claim 6 wherein the communication cable transmits low-voltage DC power.

8. An apparatus as recited in claim 6 wherein each of the first and second conductor wires are constituents of a twisted pair of wires.

9. An apparatus as recited in claim 6 wherein the processor further issues signals to measure resistance values for at least three of the wires of the first and second wire pairs.

10. An apparatus as recited in claim 6 wherein the communication cable is a shielded cable.

11. An apparatus as recited in claim 6 wherein the communication cable is a Power over Ethernet (PoE) cable.

12. An apparatus as recited in claim 6 wherein at least one of the wires used in either of the first or second loop measurement value is a wire shield.

\* \* \* \* \*